United States Patent [19]

Sogawa et al.

[11] Patent Number: 4,809,704
[45] Date of Patent: Mar. 7, 1989

[54] CATHETER TYPE SENSOR

[75] Inventors: Ichiro Sogawa; Taketsune Morikawa; Koro Yotsuya; Masanori Nishiguchi; Munekazu Imamura; Yasuhiko Shirakura, all of Osaka, Japan

[73] Assignee: Sumitomo Electric Industries, Ltd., Osaka, Japan

[21] Appl. No.: 35,910

[22] Filed: Apr. 8, 1987

[30] Foreign Application Priority Data

Apr. 10, 1986 [JP] Japan .................................. 61-83116

[51] Int. Cl.$^4$ ............................................. A61B 5/02
[52] U.S. Cl. ..................................... 128/675; 128/635
[58] Field of Search ................ 128/635, 672, 675, 748

[56] References Cited

U.S. PATENT DOCUMENTS

| | | | |
|---|---|---|---|
| 3,831,588 | 8/1974 | Rindner | 128/675 |
| 4,023,562 | 5/1977 | Hynecek | 128/675 X |
| 4,191,193 | 3/1980 | Seo | 128/675 |
| 4,218,298 | 8/1980 | Shimeda et al. | 128/635 X |
| 4,274,423 | 6/1981 | Mizuno et al. | 128/675 |
| 4,409,980 | 10/1983 | Yano et al. | 128/635 |
| 4,694,834 | 9/1987 | Meyerhoff et al. | 128/635 |

FOREIGN PATENT DOCUMENTS

| | | |
|---|---|---|
| 2708607 | 2/1977 | Fed. Rep. of Germany . |
| 215467 | 11/1984 | Fed. Rep. of Germany ...... 128/748 |
| 234559 | 4/1986 | Fed. Rep. of Germany ...... 128/748 |
| 8302952 | 3/1985 | Netherlands .......................... 128/675 |

OTHER PUBLICATIONS

EP 87 30 3109 European Search Report, 8056 Journal of Physics E. Scientific Instruments, vol. 16 (1983) "Medical Applications of Silicon Sensors".

Primary Examiner—Lee S. Cohen
Attorney, Agent, or Firm—Cushman, Darby & Cushman

[57] ABSTRACT

A catheter type sensor, which is inserted into a living body in order to directly measure within the living body biological data such as blood pressure, has at least one base in its distal end or intermediate portion, at least one sensor element supported on the base to detect biological data, and lead wires for electrically connecting together the sensor element and an external measuring device. The base, the sensor element and the lead wires are buried in a resin material which has excellent compatibility with living bodies and which is shaped in the form of a catheter. Accordingly, the whole of the cross-sectional area of the sensor can be utilized as a space for mounting the assembly constituted by the base, the sensor element and the lead wires.

10 Claims, 3 Drawing Sheets

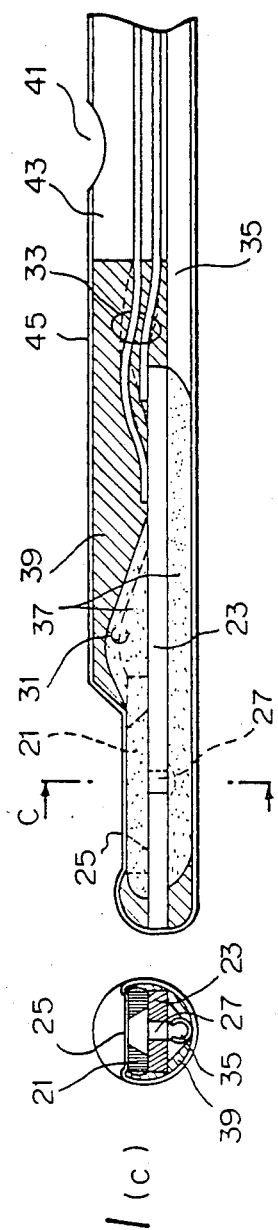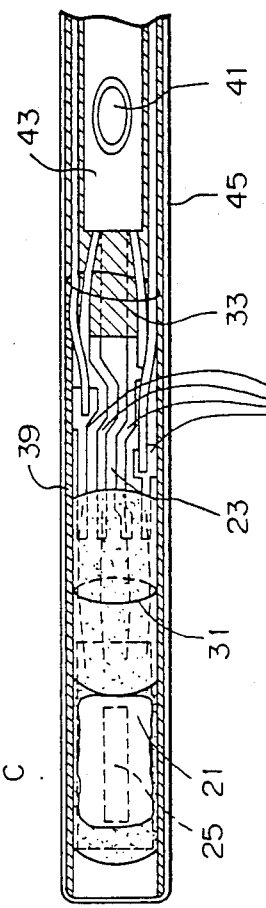
Fig. 1(a)
Fig. 1(b)
Fig. 1(c)

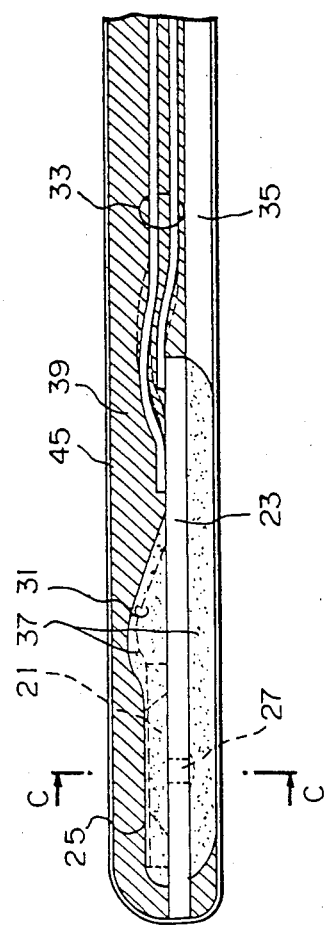
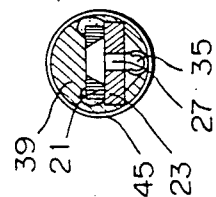
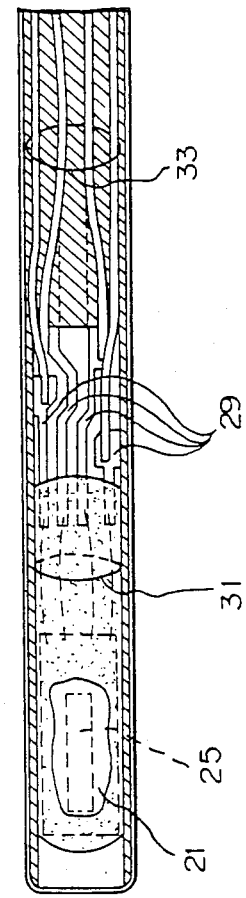
Fig. 2(a)
Fig. 2(b)
Fig. 2(c)

CATHETER TYPE SENSOR

BACKGROUND OF THE INVENTION

1. Field of the Invention

The present invention relates to a catheter which is inserted into a living body, for example, a blood vessel, in order to directly measure within the living body biological data such as blood pressure, the pH of the blood and the saturation degree of oxygen in the blood.

2. Description of the Prior Art

A typical conventional catheter which is inserted into, for example, a blood vessel to measure biological data such as blood pressure, the pH of the blood and the saturation degree of oxygen in the blood has an arrangement such as that shown in FIGS. 3(a) and 3(b). More specificlly, a sensor element 1 for detecting biological data such as blood pressure, a base 3 for supporting the sensor element 1 and lead wires 5 for electrically connecting the sensor element 1 to an external measuring device (not shown) are assembled together in advance, inserted into the bore in a sheathing tube 7 which is fabricated in advance, and positioned in such a manner that the sensitive surface of the sensor element 1 faces a measuring window 9 provided in the tube 7. In this state, the gap between the tube 7 and the assembly constituted by the sensor element 1, the base 3 and the lead wires 5 is filled with a sealing resin 11, as also is the distal end portion of the tube 7, the assembly thereby being secured in position within the tube 7 and a catheter thus being completed. In some cases, a sensor protecting film 13 is provided over the measuring window 9 so as to protect the sensitive surface of the sensor element 1.

The conventional catheter suffers, however, from the following problems. Namely, since the assembly which is constituted by the sensor element 1, the base 3 and the lead wires 5 is inserted into the bore in the sheathing tube 7, the space which could be effectively utilized for mounting the assembly is narrowed by the wall thickness of the tube 7. More specifically, the effective cross-sectional area which can be used to mount the assembly is what remains after subtraction of the wall thickness of the tube 7 from the total cross-sectional area determined by the outermost diameter of the catheter, i.e. the tube, which means that the cross-sectional area of the tube 7 cannot be utilized effectively. In the above-described structure of the conventional catheter the wall thickness of the tube 7 cannot be reduced to any great extent since the greater part of the structural strength required of a catheter depends on the strength of the tube 7, and it is therefore impossible to utilize the relatively thick wall portion of the tube 7 for mounting the assembly. Accordingly, it has been difficult to cope with the need to reduce the diameter of the catheter, to assemble together a plurality of kinds of sensor elements in order to form a composite sensor means without substantially increasing the outer diameter of the catheter, or to incorporate a tube for injection of a medical fluid or for collection of blood in the above-described arrangement so as to provide a multifunctional catheter without substantially increasing the outer diameter of the catheter.

SUMMARY OF THE INVENTION

In view of these circumstances, it is a primary object of the present invention to provide a catheter which is free from the above-described disadvantages of the prior art.

To this end, the present invention provides a catheter having at least one base in its distal end or intermediate portion, at least one sensor element supported on the base to detect biological data, and lead wires for electrically connecting together the sensor element and an external measuring device, wherein the base, the sensor element and the lead wires are buried in a resin material which exhibits excellent compatibility with living bodies and which is shaped in the form of a catheter.

By virtue of the above-described arrangement, since the assembly constituted by the sensor element, the base and the lead wires are rigidly buried in a resin material shaped in the form of a catheter, the resin material has no bore such as that of the conventional armoring tube and the whole cross-sectional area of this resin material can be utilized as a space available for mounting the assembly, and it is therefore possible for the catheter according to the present invention to provide a larger mounting space than that of the conventional catheter, provided that the sensors have the same outer diameter. Accordingly, it is possible to readily cope with the need to provide a catheter having a composite sensor means or a multiplicity of functions and also possible to reduce the outer diameter of the sensor as compared with the conventional catheter having the same size.

The above and other objects, features and advantages of the present invention will become more apparent from the following description of the preferred embodiments thereof, taken in conjunction with the accompanying drawings.

BRIEF DESCRIPTION OF THE DRAWINGS

FIGS. 1(a) and 1(b) are longitudinal vertical and horizontal sectional views, respectively, of one embodiment of the catheter according to the present invention;

FIG. 1(c) is a sectional view taken substantially along the line C—C of FIG. (a);

FIG. 2(a), 2(b) and 2(c) show in combination another embodiment of the catheter according to the present invention, which are similar to FIGS. 1(a), 1(b) and 1(c), respectively;

BRIEF DESCRIPTION OF THE DRAWINGS

Figures 3A, 3B:
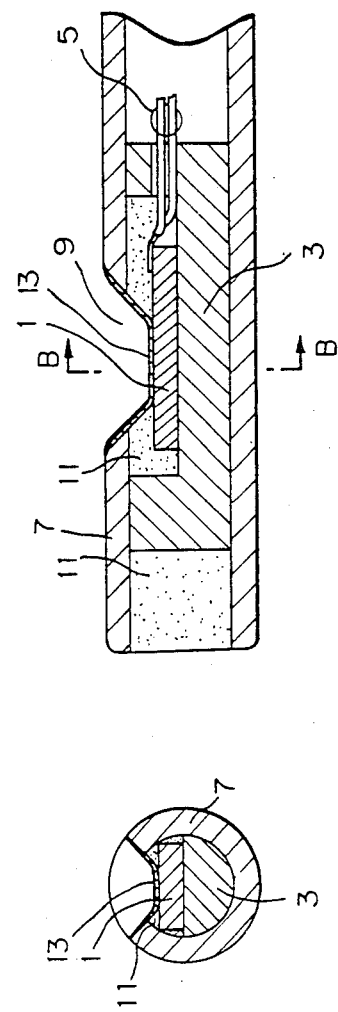
FIG. 3(a) is a longitudinal vertical sectional view of one example of conventional catheters and FIG. 3(b) is a sectional view taken substantially along the line B—B of FIG. 3(a).

Preferred embodiments of the present invention will be described hereinunder the detail.

FIGS. 1(a), 1(b) and 1(c) show in combination one embodiment of the present invention which is formed as a catheter adapted to be inserted into a blood vessel for direct measurement of blood pressure.

Referring to FIG. 1, a semiconductor diaphragm type pressure sensor element 21 is rigidly welded to the surface of a long plate-shaped base 23 using a gold-silicon alloy, the base 23 being made from a sintered material containing aluminum oxide as its principal component. The reason why such a sintered material is employed to form the base 23 is that this kind of sintered material has heretofore been used to form packages for semiconductor IC's and it is therefore possible to use existing IC packaging techniques to package the sensor element 21, and also that said sintered material is stable in vivo. The base 23 has an air vent 27 which communicates with the space defined at the rear side of the diaphragm 25 of the sensor element 21. The base 23 also has wiring patterns 29 printed on its surface for the purpose of electrically connecting therethrough the sensor element 21 to an external measuring device (not shown). More specifically, the sensor element 21 and the wiring patterns 29 formed on the base 23 are connected by means of bonding wires 31, whereas the wiring patterns 29 and lead wires 33, e.g., enamelled wires, which are connected to the external measuring device are connected by means of soldering. It is preferable to adopt wedge bonding in order to lower the loop height at the wire connection and to thereby enable a further reduction in the outer diameter of the catheter in its final assembled state.

The sensor element 21 may electrically detect the degree to which the diaphragm 25 is deflected in accordance with the level of blood pressure, and it is necessary to maintain the reverse side of the diaphragm 25 under atmospheric pressure in order to measure blood pressure with the atmospheric pressure used as a reference. For this purpose, one end of an air vent tube 35 is connected to the air vent 27 in the base 23 which communicates with the space defined at the rear side of the diaphragm 25, and the other end of the tube 35 opens into the atmosphere. The sensor element 21, the bonding wires 31 and the base 23 are coated with a protection resin material 37 for the purposes of maintaining the airtight sealing connection between the sensor element 21, the air vent 27 in the base 23 and the air vent tube 35, of supporting and reinforcing the bonding wires 31 and of forming round portions at the corners of sensor element 21.

Thus, the sensor element 21, the base 23 and the lead wires 33 are connected, together with the air vent tube 35, and are coated with the protection resin material 37. This assembly is then shaped in the form of the distal end portion of a catheter by an integral molding technique using a molding resin material 39 in such a manner that the surface of the diaphragm 25 of the sensor element 21 is exposed. It is preferable to employ urethane or silicone resin material which has excellent compatibility with a living body as the molding resin material 39. In this molding process, a lumen 43 having an opening 41 may be formed in the molded article for the purpose of collection of blood or injection of a medical fluid. It should be noted that the whole surface of the catheter including the surface of the sensor element 21 is preferably coated with a urethane resin material 45 for the purpose of further improving its compatibility with living bodies and of protecting the whole of the catheter.

The catheter thus arranged is inserted into a blood vessel to output an electric signal representing the blood pressure applied to the diaphragm 25 so as to measure the blood pressure by means of the external measuring device with the atmospheric pressure as a reference. According to this embodiment, all the constituent parts such as the sensor element 21, the base 23 and the lead wires 33 are buried within the molding resin 39 that is shaped in the form of the distal end portion of a catheter, and the molding resin is capable of providing enough strength required for a catheter in a minimum amount which is required to bury the constituent parts such as the sensor element 21. Accordingly, it is possible to considerably reduce the cross-sectional dimensions as compared with the conventional catheter.

FIGS. 2(a), 2(b) and 2(c) show in combination another embodiment of the present invention arranged as a catheter which is most suitable for measuring central venous pressure (for example, in a case where the catheter is inserted into a vein in the arm to measure blood pressure). In FIG. 2, the same reference numerals as those used in connection with the above-described embodiment denote similar constituent parts.

Since the blood flow velocity in the vein is relatively low, the blood readily coagulates to adhere to the outside of the catheter. Therefore, the catheter needs to have an outer shape which is as smooth as possible and has a uniform cross section. Further, since the rate of change with time of the venous pressure is relatively low (the measured pressure may almost be considered to be a static pressure), the measuring system is not required to respond quickly. Accordingly, the catheter in accordance with this embodiment is arranged so that the cross-sectional shape is circular throughout, including the peripheral portion of the sensor element 21, as illustrated. Although in this case the peripheral portion of the sensor element 21 is coated with a relatively thick layer of resin, there is no problem because high frequency response is not required as mentioned above. It should be noted that the portion around the sensor element 21 which is disposed at the distal end of the catheter is preferably formed from a particularly soft resin material so that the sensitivity of the sensor element 21 is improved and insertion of the catheter into blood vessels is facilitated.

Although in the above-described embodiments the sensor element 21 and the lead wires 33 are connected together through the wiring patterns 29 formed on the base 23, the lead wires 33 may also be electrically connected directly to the sensor element 21. In addition, it is possible to appropriately change the number of sensor elements 21 and bases 23 which can be mounted on a single catheter.

As has been described above, it is possible, according to the present invention, to provide a catheter having a smaller outer diameter than that of the conventional one. Since the catheter according to the present invention has a larger space for mounting sensor constituent parts than that of the conventional one provided that these catheters have the same outer diameter, it is possible to readily cope with the need to provide a catheter having a composite sensor means or a multiplicity of functions.

Although the present invention has been described through specific terms, it should be noted here that the described embodiments are not necessarily limitative and that various changes and modifications may be made without departing from the scope of the invention which is limited solely by the appended claims.

We claim:

1. A catheter comprising:
   a detecting portion including a base, at least one sensor element supported on said base for detecting biological data, and a biocompatible resin material in which said base and said sensor element are embedded; and
   an elongated body portion supporting said detecting portion and including means for transmitting data between said sensor element and an external measuring device, and a biocompatible resin material in which said data transmitting means are embedded;
   said detecting portion being defined at one of a distal end and an intermediate portion of said elongated body portion, said resin materials of said detecting portion and of said elongated body portion being integral so as to define the exterior surface of a catheter.

2. A catheter according to claim 1, wherein said resin materials are a urethane or silicone resin material.

3. A catheter according to claim 1, wherein said base is formed from a sintered material which contains aluminum oxide as its principal component.

4. A catheter according to claim 1, wherein said sensor element is a semiconductor diaphragm type pressure sensor.

5. A catheter according to claim 4, wherein said semiconductor diaphragm type pressure sensor is welded to the surface of said base using a gold-silicon alloy.

6. A catheter according to claim 1, wherein said sensor element is a pressure-sensitive element, and a portion of said catheter which is to be inserted into a living body has a substantially uniform cross-sectional shape, including the peripheral portion of said pressure-sensitive element.

7. A catheter to claim 6, wherein the portion around said pressure-sensitive element alone is coated with a particulary soft resin material.

8. A catheter according to claim 7, wherein said pressure-sensitive element is a semiconductor diaphragm type pressure sensor.

9. A catheter according to claim 1, wherein said data transmitting means includes lead wires for electrically connecting said sensor element and said external measuring device.

10. A catheter according to claim 9, wherein said sensor element is connected to the external measuring device through a wiring pattern formed by printing on a surface of said base, the electrical connection between said wiring pattern on said base and said sensor element being effected by wiring bonding, and the electrical connection between said wiring pattern and said lead wires being effected by soldering.

* * * * *